United States Patent
Ikeda

(10) Patent No.: US 10,674,712 B2
(45) Date of Patent: Jun. 9, 2020

(54) MOUNTING BEHAVIOR DETECTION SYSTEM

(71) Applicant: KYOCERA Corporation, Kyoto (JP)

(72) Inventor: Tomoyoshi Ikeda, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 270 days.

(21) Appl. No.: 15/576,891

(22) PCT Filed: May 24, 2016

(86) PCT No.: PCT/JP2016/002518
§ 371 (c)(1),
(2) Date: Nov. 27, 2017

(87) PCT Pub. No.: WO2016/189862
PCT Pub. Date: Dec. 1, 2016

(65) Prior Publication Data
US 2018/0146646 A1  May 31, 2018

(30) Foreign Application Priority Data

May 28, 2015 (JP) ................................ 2015-108863
May 28, 2015 (JP) ................................ 2015-108864

(51) Int. Cl.
*A01K 29/00* (2006.01)
*H02J 50/10* (2016.01)
(Continued)

(52) U.S. Cl.
CPC .......... *A01K 29/005* (2013.01); *A01K 11/006* (2013.01); *A01K 29/00* (2013.01);
(Continued)

(58) Field of Classification Search
CPC ..... A01K 11/006; A01K 29/005; A61D 17/004
See application file for complete search history.

(56) References Cited

U.S. PATENT DOCUMENTS 4,846,106 A  7/1989  Leonardo
5,857,434 A  1/1999  Andersson
(Continued)

FOREIGN PATENT DOCUMENTS

JP  S63-192437 A  8/1988
JP  H06-141385 A  5/1994
(Continued)

OTHER PUBLICATIONS

International Search Report issued in PCT/JP2016/002518; dated Aug. 16, 2016.
(Continued)

*Primary Examiner* — Monica L Barlow
(74) *Attorney, Agent, or Firm* — Studebaker & Brackett PC

(57) ABSTRACT

Mounting behavior is detected easily. A mounting behavior detection system includes a mounting-side apparatus, a mounted-side apparatus, and a charging apparatus. The mounting-side apparatus is attached to the neck or the chin of a first domestic animal, is configured to emit a transmission signal, and includes a battery. The mounted-side apparatus is attached at any position from the back to the tail of a second domestic animal and is configured to transmit a response signal in response to the transmission signal. The charging apparatus is configured to transmit power wirelessly to the battery.

12 Claims, 10 Drawing Sheets

(51) Int. Cl.

| | | |
|---|---|---|
| *A01K 67/00* | (2006.01) | |
| *H02J 7/00* | (2006.01) | |
| *A01K 67/02* | (2006.01) | |
| *H02J 50/80* | (2016.01) | |
| *A01K 11/00* | (2006.01) | |
| *H02J 7/02* | (2016.01) | |
| *G06K 19/077* | (2006.01) | |

(52) U.S. Cl.
CPC .............. *A01K 67/00* (2013.01); *A01K 67/02* (2013.01); *H02J 7/00* (2013.01); *H02J 7/025* (2013.01); *H02J 50/10* (2016.02); *H02J 50/80* (2016.02); *G06K 19/07783* (2013.01)

(56) References Cited

U.S. PATENT DOCUMENTS

| | | | |
|---|---|---|---|
| 6,049,280 A | | 4/2000 | Andersson |
| 6,342,041 B1 | | 1/2002 | Saint-Ramon et al. |
| 8,662,021 B2 | | 3/2014 | Gustafsson |
| 2009/0056637 A1 | | 3/2009 | Gustafsson |
| 2014/0338447 A1 | * | 11/2014 | Sharpe ................. A01K 29/005 73/431 |
| 2017/0367305 A1 | * | 12/2017 | Castro Lisboa ....... A61D 17/00 |

FOREIGN PATENT DOCUMENTS

| | | |
|---|---|---|
| JP | H10-501618 A | 2/1998 |
| JP | H11-032609 A | 2/1999 |
| JP | 2000-157084 A | 6/2000 |
| JP | 2003-189751 A | 7/2003 |
| JP | 2003-325077 A | 11/2003 |
| JP | 2004-057069 A | 2/2004 |
| JP | 2004-337093 A | 12/2004 |
| JP | 2005-210927 A | 8/2005 |
| JP | 2006-075090 A | 3/2006 |
| JP | 2007-075043 A | 3/2007 |
| JP | 2008-022760 A | 2/2008 |
| JP | 2008-206412 A | 9/2008 |
| JP | 2008-538918 A | 11/2008 |
| JP | 4368209 B2 | 11/2009 |
| JP | 2011-045284 A | 3/2011 |
| JP | 2012-090604 A | 5/2012 |
| JP | 2013-179875 A | 9/2013 |
| JP | 2015-082978 A | 4/2015 |
| WO | 2008/136060 A1 | 11/2008 |
| WO | WO-2008136060 A1 * 11/2008 ........... A01K 11/008 |

OTHER PUBLICATIONS

Written Opinion issued in PCT/JP2016/002518; dated Aug. 16, 2016; with English language Concise Explanation.

* cited by examiner

FIG. 11

Name of targeted cow:A

Mounting communication log
8:09:00 (mounting cow, mounted cow)=(A, D1R)
8:09:02 (mounting cow, mounted cow)=(A, D2R)

8:16:24 (mounting cow, mounted cow)=(A, D1M)
8:16:28 (mounting cow, mounted cow)=(A, D1M)
8:20:10 (mounting cow, mounted cow)=(A, S3M)
8:20:13 (mounting cow, mounted cow)=(A, S3L)

8:46:03 (mounting cow, mounted cow)=(A, C1R)
8:57:31 (mounting cow, mounted cow)=(A, C4L)

Mounted communication log
9:09:00 (mounting cow, mounted cow)=(D, A1R)
9:09:03 (mounting cow, mounted cow)=(D, A5L)
9:14:45 (mounting cow, mounted cow)=(D, A2L)
9:14:47 (mounting cow, mounted cow)=(C, A3L)

FIG. 12

Name of targeted cow:A

- Place emergency call (090-1234-5678)
  to veterinarian (Dr. xxx)?

[YES]  [NO]

- Transmit information on mounting behavior
  to veterinarian (Dr. xxx)?

[YES]  [NO]

- Instruct veterinarian (Dr. xxx) to conduct
  artificial insemination?

[YES]  [NO]

- Continue to observe?

[YES]  [NO]

MOUNTING BEHAVIOR DETECTION SYSTEM

CROSS-REFERENCE TO RELATED APPLICATIONS

The present application claims priority to and the benefit of Japanese Patent Application Nos. 2015-108863 and 2015-108864 filed May 28, 2015, the entire contents of which are incorporated herein by reference.

TECHNICAL FIELD

The disclosure relates to detection of mounting behavior or the like by domestic animals or the like.

BACKGROUND

Conventionally, a technique of detecting recumbence and standing when a cow is in heat (estrus) by communication between a radio-frequency identification (RFID) tag worn below a cow's abdomen and a reader/writer apparatus installed in a cattle shed is known.

Conventionally, a technique of detecting the mounting behavior of a cow in heat by detecting inclination with an acceleration sensor is known.

Conventionally, a technique of using an inclination sensor to detect recumbence and standing when a cow is in heat is known.

Conventionally, a technique of detection of heat by using a walking sensor to detect the number of steps a cow takes is known.

Conventionally, a technique of detection of heat by using a motion sensor to detect the amount of activity of a cow is known.

Conventionally, a technique of detection of heat by installing a reader/writer apparatus in a cattle shed and attaching a tag, such as an RFID, to a cow to detect the walking distance of the cow is known.

Conventionally, a technique of detection of heat by detecting movement by a cow with a movement sensor and a transmitter that transmits a signal from the movement sensor is known.

Conventionally, a technique of detection of heat by using a walking sensor to detect the number of steps a cow takes is known.

Conventionally, a technique of detection of heat by using a vibration sensor to detect the amount of activity of a cow is known.

Conventionally, a technique of detection of heat by using a walking sensor to detect the number of steps a cow takes is known.

Conventionally, a technique of detection of heat by using a pressure sensor attached to a cow's waist to detect the mounting behavior of the cow is known.

Conventionally, a technique of detection of heat by using a pressure responsive switch attached to a cow's spine to detect the mounting behavior of the cow is known.

Conventionally, a technique of the structure of a mounting fixture of a detection device for detecting the mounting behavior of a cow by using a pressure sensor attached to the cow's spine is known.

Conventionally, a technique of providing notification by light upon detecting mounting behavior of a cow with a pressure sensor attached to the cow is known.

Conventionally, a technique of the structure of a mounting fixture of a detection device for detecting the mounting behavior of a cow by using an acceleration sensor or an inclination sensor attached to the cow's backbone is known.

Conventionally, a technique of detecting recumbence and standing when a cow is in heat with a temperature sensor that detects the cattle shed temperature is known.

Conventionally, a technique of detecting that a cow is in heat with a temperature sensor that detects the temperature of the cow's vagina is known.

Conventionally, a technique of transmitting ultrasonic waves from an ultrasonic transmitter attached to the neck of one cow to an ultrasonic receiver attached to the neck of another cow and having the ultrasonic receiver attached to the neck of the other cow receive the ultrasonic waves is known. Conventionally, a technique that the number of times ultrasonic waves are received is counted directly as the number of times the cow mounts (is mounted), i.e. the mounting (mounted) count is also known. Conventionally, a technique of the use of electromagnetic waves or infrared rays instead of ultrasonic waves is also known.

SUMMARY

A mounting behavior detection system according to an embodiment of the disclosure includes:
  a mounting-side apparatus attached to a neck or a chin of a first domestic animal, configured to emit a transmission signal, and including a battery;
  a mounted-side apparatus attached at any position from a back to a tail of a second domestic animal and configured to transmit a response signal in response to the transmission signal; and
  a charging apparatus configured to transmit power wirelessly to the battery.

A mounting behavior detection system according to an embodiment of the disclosure includes:
  a mounting-side apparatus attached to a neck or a chin of a first domestic animal and configured to emit a transmission signal; and
  a mounted-side apparatus attached at any position from a back to a tail of a second domestic animal and configured to transmit a response signal in response to the transmission signal; wherein
  the mounting-side apparatus is sealed by a sealing member.

BRIEF DESCRIPTION OF THE DRAWINGS

In the accompanying drawings:

FIG. 11 illustrates an example of a screen on the user-side apparatus in the detection system;

FIG. 12 illustrates an example of a screen on the user-side apparatus in the detection system;

DETAILED DESCRIPTION

The disclosure proposes a system for easily detecting mounting behavior and incidents of being mounted when a female cow is in heat.

(Solution to Problem)

An embodiment of the disclosure is described below with reference to the drawings, which illustrate various examples. These examples may be applied to each other or modified in any logically coherent way. Various techniques may also be added or modified in any logically coherent way.

Figure 1:
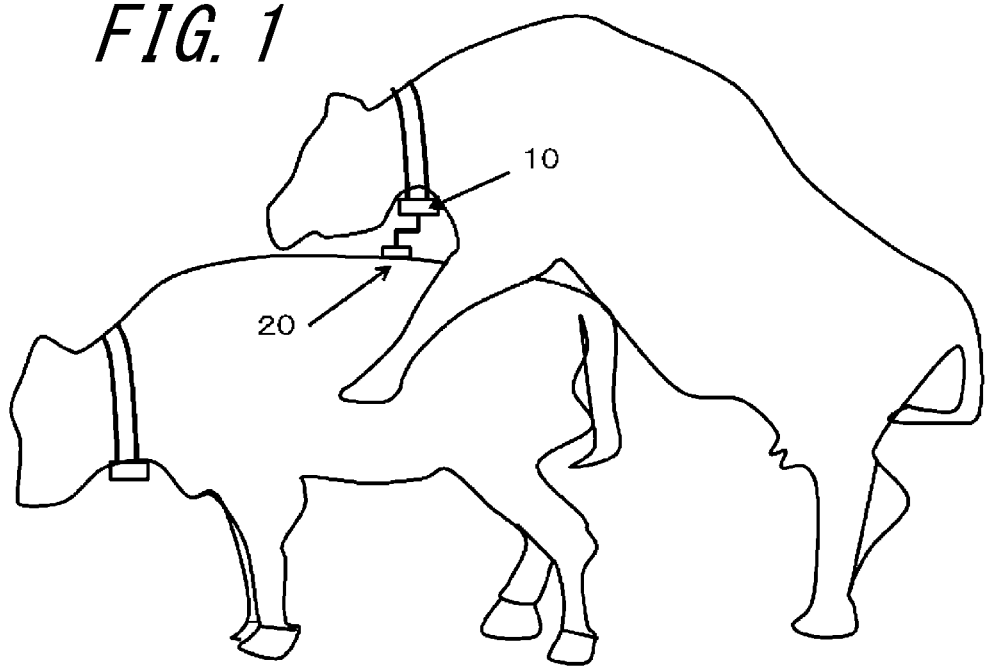
FIG. 1 is an overview of a detection system.

FIG. 1 illustrates an overview of the detection system with a usage example. Here, a mounting-side apparatus 10 is attached to the throat or neck of the mounting cow, and one mounted-side apparatus 20 is attached by the withers of the mounted cow (the term "cow" as used herein may refer to either a cow or a bull, unless otherwise specified). The mounting-side apparatus 10 periodically transmits a transmission signal (electromagnetic waves or radio waves). Once the mounted-side apparatus 20 faces the mounting-side apparatus 10 at an appropriate distance, such as 0 cm to 30 cm, the mounted-side apparatus 20 receives the transmission signal from the mounting-side apparatus 10. With a transmission signal received from the mounting-side apparatus 10 as a trigger (or upon receiving energy from a transmission signal), the mounted-side apparatus 20 responds to the mounting-side apparatus 10 with a response signal constituted by a unique ID of the mounted cow, the ID being stored in the mounted-side apparatus 20. During mounting behavior, the area around the throat, neck, or dewlap of the mounting domestic animal (for example, a cow) often faces the mounted cow's back and the area further behind, i.e. the hips, buttocks, or tail (not the head or throat). In the disclosure, "faces" also includes the case of actual contact. Therefore, the mounting-side apparatus 10 and the mounted-side apparatus 20 may be, for example, attached at such facing positions.

A female cow in heat is also known to rest its chin on another cow's back, hips, buttocks, or the like (chin resting). In this case as well, the mounting-side apparatus 10 disposed at the throat or below the neck faces the mounted-side apparatus 20 on the back. As above, reception of the signal from the mounting-side apparatus 10 serves a trigger for the mounted-side apparatus 20 to respond to the mounting-side apparatus 10 with the unique ID, stored in the mounted-side apparatus 20, of the mounted cow.

In this way, the mounted-side apparatus 20 transmits the unique ID of the mounted cow to the mounting-side apparatus 10 of the mounting cow. Together with the mounting cow's unique ID stored in the mounting cow's mounting-side apparatus 10, the combination of the mounting cow and the mounted cow can be detected. Accordingly, the mounting-side apparatus 10 may notify a user of the unique ID of a cow involved in mounting behavior (the mounting cow or the mounted cow) and/or of detection of a combination of cows involved in mounting behavior. The mounting-side apparatus 10 may, for example, notify the user by emission of light from a notification interface 11 such as an LED attached to the mounting-side apparatus 10 or by emission of sound from a notification interface 11 such as a buzzer.

Figure 2:
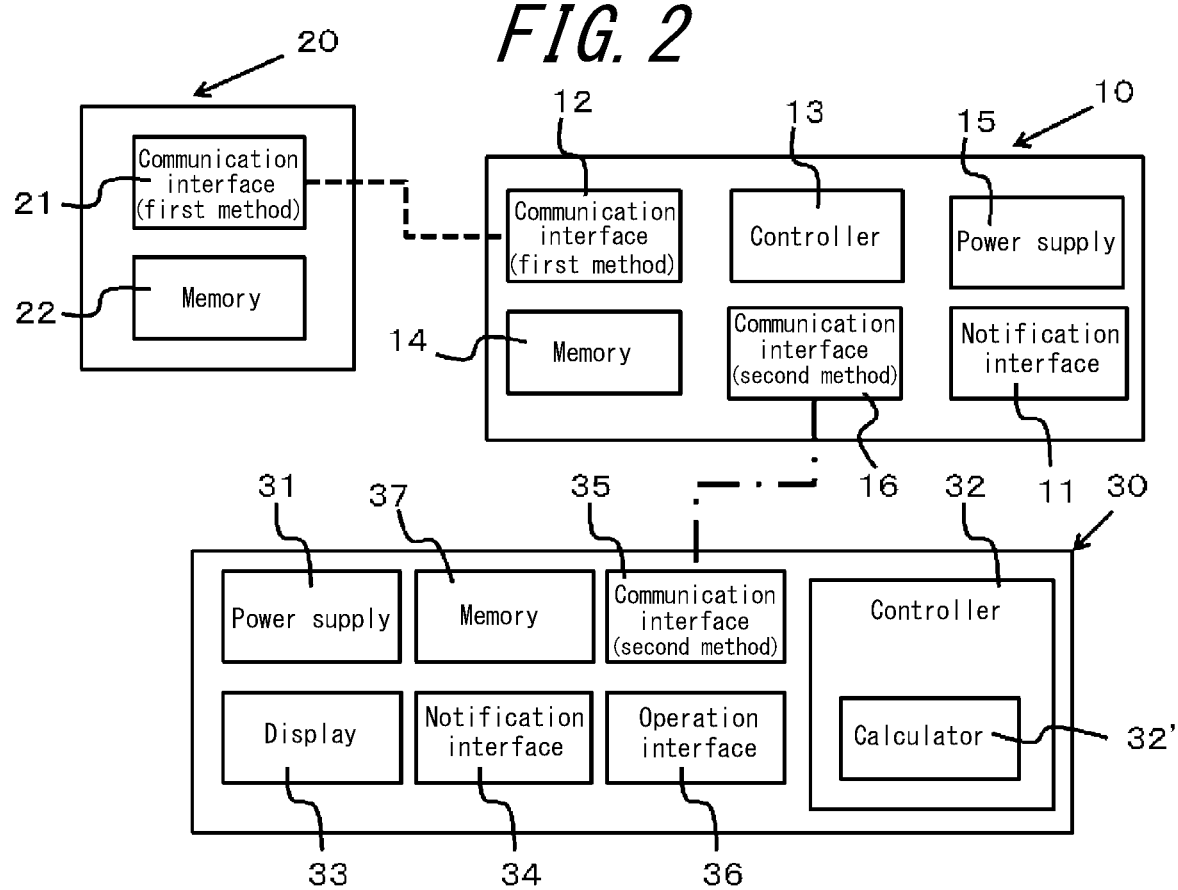
FIG. 2 is a functional block diagram of an example of the detection system.

Next, with reference to FIG. 2, an example configuration of the detection system is described. In the detection system of FIG. 2, the mounting-side apparatus 10, the mounted-side apparatus 20, and a user-side terminal 30 may be included.

The mounting-side apparatus 10 emits a signal to the mounted-side apparatus 20 by a first communication method (first method) and receives a response from the mounted-side apparatus 20 by the first communication method. For example, the first method is a communication technique such as radio-frequency identification (RFID) (for example, near field communication (NFC) (NFC-A, NFC-B, NFC-F)) or a communication method with high directivity, such as infrared data association (IrDA).

In the case of using the reader/writer apparatus used with an NFC technique as the first communication method, the mounting-side apparatus 10 transmits an electromagnetic wave that becomes a transmission signal to the mounted-side apparatus 20, which includes a tag (mainly constituted by an antenna and a memory) referred to as a passive RFID tag. The electromagnetic wave that becomes the transmission signal may also serve as an energy source for responding. The mounting-side apparatus 10 also includes the notification interface 11, a communication interface 12, compliant with NFC (NFC-A, NFC-B, NFC-F, or the like), for receiving a signal (response) from the RFID tag of the mounted-side apparatus 20, a controller 13, a memory 14 storing the unique ID of the domestic animal (female cow, calf, horse, pig) to which the mounting-side apparatus 10 is attached, a power supply 15 for which a battery (secondary cell), fuel cell, or the like can be used, and (in the case of the below-described user-side terminal 30 being included) a communication interface 16, compliant with a second communication method (for example, code division multiple access (CDMA), long-term evolution (LTE), WiFi, BlueTooth® (BlueTooth is a registered trademark in Japan, other countries, or both), or the like), for allowing communication with the user-side terminal 30. At a minimum, it suffices for the content of the transmission signal to be a request for return of the unique ID stored in the memory of the mounted-side apparatus 20.

Instead of an NFC technique, IrDA may also be adopted for the first method. In this case, it suffices for the communication interface 12 of the first method to include an optical emitter and an optical detector that respectively emit and detect infrared rays. IrDA has the advantage of a greater communicable range (approximately 30 cm to 1 m) than NFC. Furthermore, instead of emission and detection of infrared rays, pulsed laser light with a specific wavelength may be emitted and detected.

The solid angle at which communication is possible with NFC, IrDA, or laser light is small, and the communication interfaces need to be in a nearly facing state. Therefore, in an embodiment of the disclosure, a communication method with high directivity may be adopted on purpose to reduce the probability of erroneous detection. This approach has the advantage of making it easy to reduce the chance of erroneous detection whereby the communication interfaces end up communicating regardless of mounting behavior or chin resting.

The communication interface 12 of the first method of the mounting-side apparatus 10 repeats transmission at approximately one-second intervals, for example. Transmission may be more frequent than once per second. Upon receiving a response while transmitting once per second, the mounting-side apparatus 10 subsequently repeats transmission over shorter cycles of one transmission approximately every 0.1 s to 0.3 s until at least a certain time (for example, at least 4 s) from the last response (mounting detection time+at least a certain time). Such transmission is for accurate measurement of the continuous mounting time while reducing power consumption when mounting is not taking place. The setting of this cycle may be changed in various ways.

The communication interface 16 of the second method may be compliant with CDMA, LTE, WiFi, or BlueTooth®, for example. The second method may have low directivity and a distance that allows transmission of radio waves from within the grazing land of the pasture to outside the grazing land. For example, it suffices for the distance to exceed approximately 200 m. This distance may be shorter when one or more relay base stations are installed in the grazing land. For example, the communication distance may be approximately several dozen meters. When using an electric pasture fence (to which a high-voltage, low-current pulsed wave is typically applied), a power line for a relay base station may further be strung along the pasture fence.

The mounted-side apparatus 20 may be configured by a tag that uses a method corresponding to the first method of the mounting-side apparatus 10, such as an NFC technique, and may include a communication interface 21 and a memory 22. It suffices for a unique ID for at least each domestic animal to which a mounted-side apparatus 20 is attached to be written in the memory 22. When the first method is NFC, the communication interface 21 may adopt a tag capable of communication in RFID communication mode. In this case, the structure for attachment to the back of a cow or other domestic animal can be simplified, since no power supply, such as a battery, is necessary. The mounted-side apparatus 20 may be provided with a battery used as a power supply to perform communication. When using IrDA or pulsed laser light as the first method, it suffices for the communication interface 21 to include a corresponding optical detector and optical emitter. The mounted-side apparatus 20 may be further provided with a power supply for driving the optical emitter.

The user-side terminal 30 may not be necessary in some cases but does increase convenience. The user-side terminal 30 may include a power supply 31, a controller 32 (calculator 32'), a display 33, a notification interface 34, a communication interface 35, an operation interface 36, and a memory 37. The apparatuses that can most easily include these components are a PC, a smartphone, a tablet, or the like (including applications that can run on these apparatuses). An outdoor-type smartphone that is resistant to moisture or to dirt and dust during work in the barn may be used as this apparatus.

The controller 32 is for overall control of the user-side terminal 30. In particular, the calculator 32' calculates a mounting count (mounting length of time) or a mounted count (mounted length of time) for each cow and compares these calculation results with respective thresholds. Details are provided below.

The display 33 may be capable of displaying information on the below-described mounting count or the like, a selection screen or the like with options such as whether to contact a veterinarian, and a screen for when an e-mail or phone call is received.

The notification interface 34 may provide notification when the mounting count, mounted count, or the like exceeds a predetermined threshold (if such functions are included) and may provide notification when an e-mail or a phone call is received. The notification may be provided in a variety of well-known ways, such as by sound, light, vibration, or text display. In particular when it is strongly suspected that a cow is in heat, or that the cow should be inseminated immediately on the basis of the elapsed time from the start of heat, the notification interface 34 may notify the user in a form with a stronger impact than usual. For example, the form of notification may be different levels of volume, different intensities of light, or the like. Alternatively, if one type of notification is normally provided, such as sound, the notification interface 34 may provide notification by a plurality of methods in the case of an emergency, such as sound along with light, vibration, or the like.

The communication interface 35 of the second method may communicate with the above-described communication interface 16 of the second method by a method compliant with any one or more of CDMA, LTE, WiFi, or BlueTooth®, for example.

A variety of techniques for receiving operations, such as operation keys or a touch panel, may be used in the operation interface 36.

The memory 37 stores information, for example, related to the mounting behavior and acquired through the communication interface 35, or may be used as a storage area during various calculation processing or the like. As a phone book function, the memory 37 may also include information on particular veterinarians or artificial inseminators, records on the physical condition and on the past heat of each cow (such as records of the past two heats and the record of the time of insemination for the past year), and the like.

Figure 3:
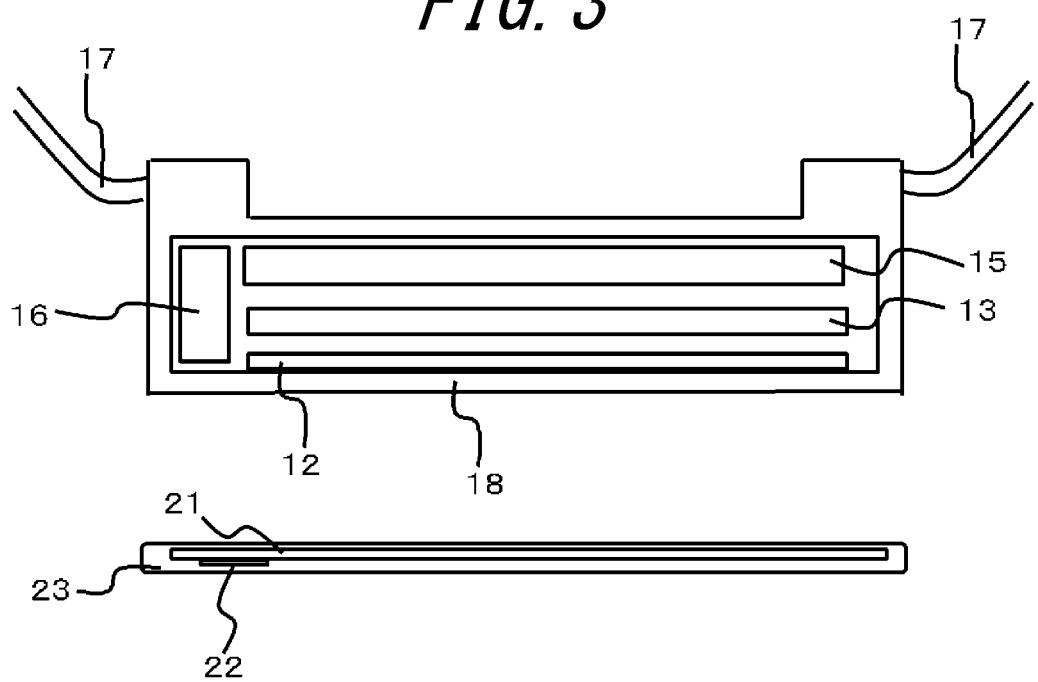
FIG. 3 is a cross-sectional diagram schematically representing an example of a mounting-side apparatus.
Figure 4:
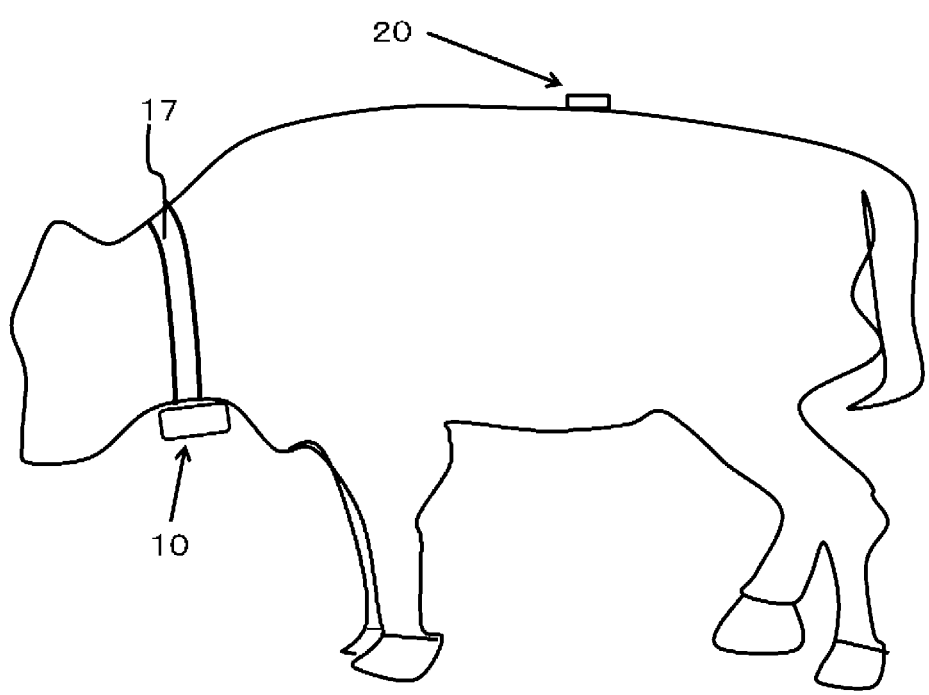
FIG. 4 illustrates an example of the mounting-side apparatus and the mounted-side apparatus being worn by a cow.
Figure 5:
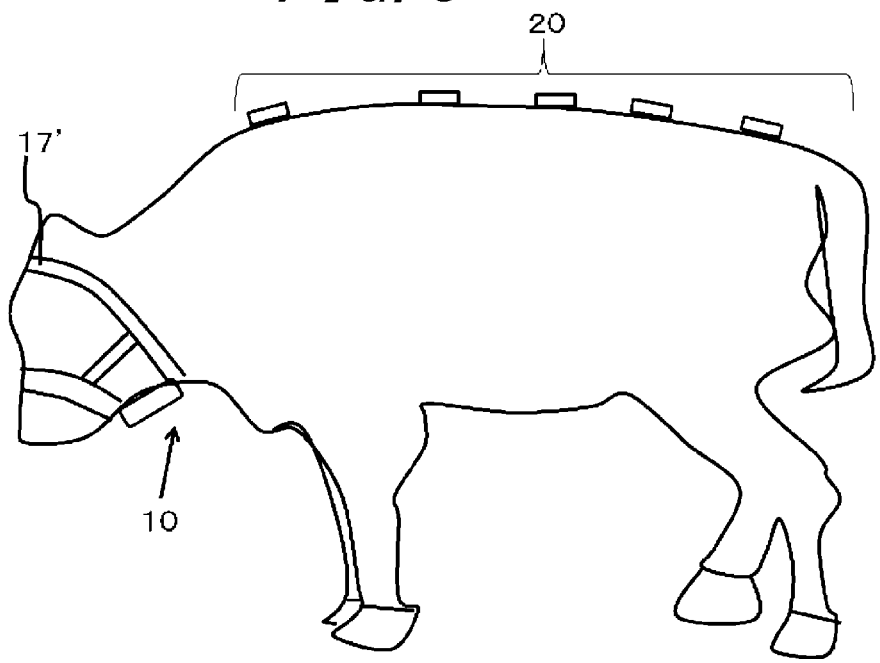
FIG. 5 illustrates an example of the mounting-side apparatus and the mounted-side apparatus being worn by a cow.

Next, with reference to FIGS. 3 through 5, several examples of the structure of the mounting-side apparatus 10 are described. As illustrated in FIG. 3, an antenna of the communication interface 12 is provided in a waterproof housing 18 as an example of the case of using an NFC technique for the first method. The antenna may be disposed on the side that is closer to the mounted cow during mounting behavior. When the first method is IrDA, the optical emitter and optical detector may also be disposed on the side closer to the mounted cow during mounting behavior. Furthermore, a circuit board may be disposed inside the housing 18 and may configure a portion or all of the controller 13 and the memory 14. A lithium-ion type or other type of power supply 15, for example, is also provided in the housing 18. An antenna for the communication interface 16 of the second method may also be provided inside the housing 18. A display, a notification interface, and the like may also be provided in the housing 18.

FIG. 3 illustrates an example configuration of the mounting-side apparatus 10 and the mounted-side apparatus 20. In the example in FIG. 3, a holder 17 is attached to the outside of the housing 18 of the mounting-side apparatus 10. The holder 17 is, for example, a collar-type holder as illustrated in FIG. 4. Alternatively, the holder 17 may, for example, be a bridle-type holder 17' as illustrated in FIG. 5. These holders may be configured by the typical constituent members of bridles or the like for domestic animals, such as rubber, leather, cloth, rope, cords, or the like, and may have durability and flexibility. A mechanism for adjusting the length may be used in each of the holder 17 and bridle 17'. When worn, the collar 17 or the bridle 17' need not be tightened until squeezing the domestic animal's neck but rather may have a length that leaves a slight gap from the neck. The holder 17 may be a crossed belt that wraps around from the domestic animal's shoulders to the front legs or may be like a girth for a horse.

The mounted-side apparatus 20 includes the communication interface 21 and the memory 22 in a film-shaped holding member 23. The communication interface 21 includes an antenna (coil) formed as a pattern on a substrate such as an FPC. The communication interface 21 and the memory 22 are sealed within the holding member 23. It suffices for the mounted-side apparatus 20 to be attached to the back or other location of a cow or the like using an attachment member.

One mounted-side apparatus 20 is provided in FIG. 4, whereas a plurality of mounted-side apparatuses 20 are provided in FIG. 5. When constituted by a loop antenna and a memory, for example as illustrated in FIG. 2, the mounted-side apparatus 20 may be a chip, called an NFC chip, measuring approximately 3 mm to 1 cm both wide and long. In this case, by providing a plurality of mounted-side apparatuses 20 on the back as illustrated in FIG. 6, the probability of mounting not being detected because of misalignment at the time of mounting is reduced.

Figure 6:
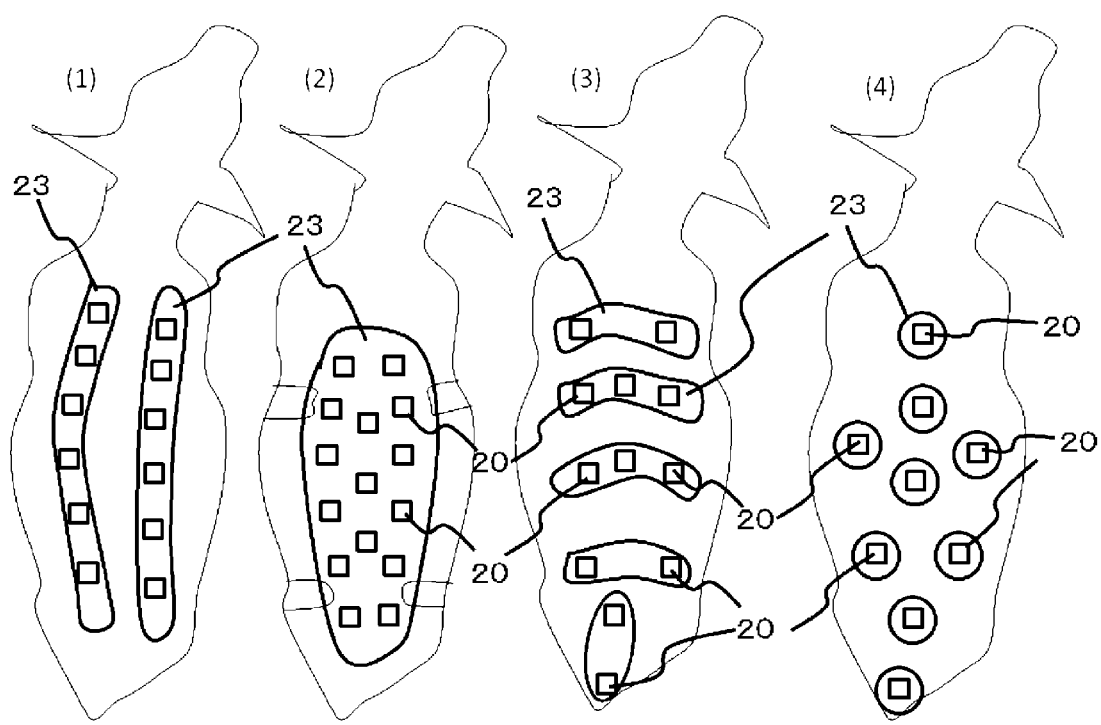
FIG. 6 illustrates examples of the mounted-side apparatus being worn by a cow.

FIG. 6 illustrates four patterns in order from the left. In the leftmost pattern (1), mounted-side apparatuses 20 are aligned on either side of a domestic animal's backbone. Here, the bands on the left and right indicate holding members 23 that hold the mounted-side apparatuses 20. In this way, the mounted-side apparatuses 20 are disposed not only on the backbone but also to the left and right, making it easier to detect chin resting. The band-shaped holding members 23 may, for example, be constituted by cloth or rubber and may be adhered to the domestic animal's back by, for example, application of adhesive. The applied adhesive may be a biocompatible medical adhesive (for example, a cyanoacrylate adhesive). It suffices for the adhesive to adhere partially to the cow or horse's hair. After a certain amount of time passes, the holding member 23 falls off with the adhesive at the time of hair loss, or the holding member 23 is collected every 21 days in accordance with the heat cycle. Therefore, regardless of type, the adhesive has little adverse effect on the domestic animal's body. When the mounted-side apparatus 20 is a type not using a battery, the mounted-side apparatus 20 need not be removed from the domestic animal every time in the detection system. If a battery is necessary, a configuration may be adopted for removal of the battery alone.

In these holding members 23, six mounted-side apparatuses 20 per side are adhered on the left and right in pattern (1) furthest to the left in FIG. 6, for a total of 12 apparatuses. With this configuration, the neck position of the mounting domestic animal or the posture at the time of mounting can easily be detected, as can variation in the position of the back and chin during chin resting. In pattern (2) illustrated in FIG. 6, the holding member 23 includes a cover and belts. The mounted-side apparatuses 20 are arranged on the cover, which is constituted by cloth, rubber, a net, or the like that covers a wide region on the back. The belts are attached to the sides of the cover and encircle the domestic animal's stomach. In this case, the mounted-side apparatus 20 may also be disposed on the portion of the withers corresponding to the backbone of the cow. The mounting-side apparatus 10 attached to the cow's neck is often disposed directly in the center, without deviating to the left or the right of the domestic animal. Hence, disposing the mounted-side apparatuses 20 in this way on the backbone makes mounting behavior less likely to be missed. Adhesive may be used instead of belts, as in pattern 1.

In pattern (3), horizontally extending bands are disposed across the backbone. Here, adhesive or a belt may be used for the material and structure of the holding members 23, as in patterns (1) and (2). Mounted-side apparatuses 20 are also disposed along the backbone at the tail head. Disposing mounted-side apparatuses 20 at the tail head as well in this way is effective when, for example, not only female cows but also male calves are grazing in the same pasture area. In other words, when the mounting-side apparatus 10 is attached to a male calf, the mounting-side apparatus 10 of the calf might not reach the withers of a female cow capable of giving birth, because the calf is short. Accordingly, by attaching the mounted-side apparatuses 20 from the female cow's hips or buttocks to near the tail, such as the tail head, the behavior of mounting (being mounted) can be detected more easily.

In pattern (4), the chip-shaped mounted-side apparatuses 20 are fixed in place using adhesive members constituted by adhesive. In other words, the holding member 23 itself may be adhesive. Here, a plurality of mounted-side apparatuses 20 is individually attached at positions likely to face the mounting-side apparatus 10, such as the domestic animal's back, hips, or tail. Instead of only being constituted by adhesive, the holding member 23 may be a slice of acrylic, PET, or the like which has adhesive attached to the back side and on which a chip is fixed. Adhesive may be used on the back face of the slice, as above, when attaching the slice of acrylic or the like to a cow's tail or skin. The holding member 23 may also be an adhesive sheet. The holding member 23 may also be an adhesive bandage or surgical tape onto which the chip of the mounted-side apparatus 20 is attached. Such a structure is simple and inexpensive. The chip and hardened adhesive may be covered with an element such as urethane gel. The risk of the mounted-side apparatus 20 or holding member 23 catching or scratching the lower abdomen or chin of the domestic animal during mounting or chin resting can thus be reduced. The holding member 23 may include such a covering member.

FIGS. 7 through 12 are examples of display screens on the display 33 of the user-side terminal 30 displaying information, collected from the mounting-side apparatus 10, on the mounting behavior of each domestic animal. With reference to the screen examples, the information on mounting behavior and algorithms for determining heat are described in order.

Figure 7:
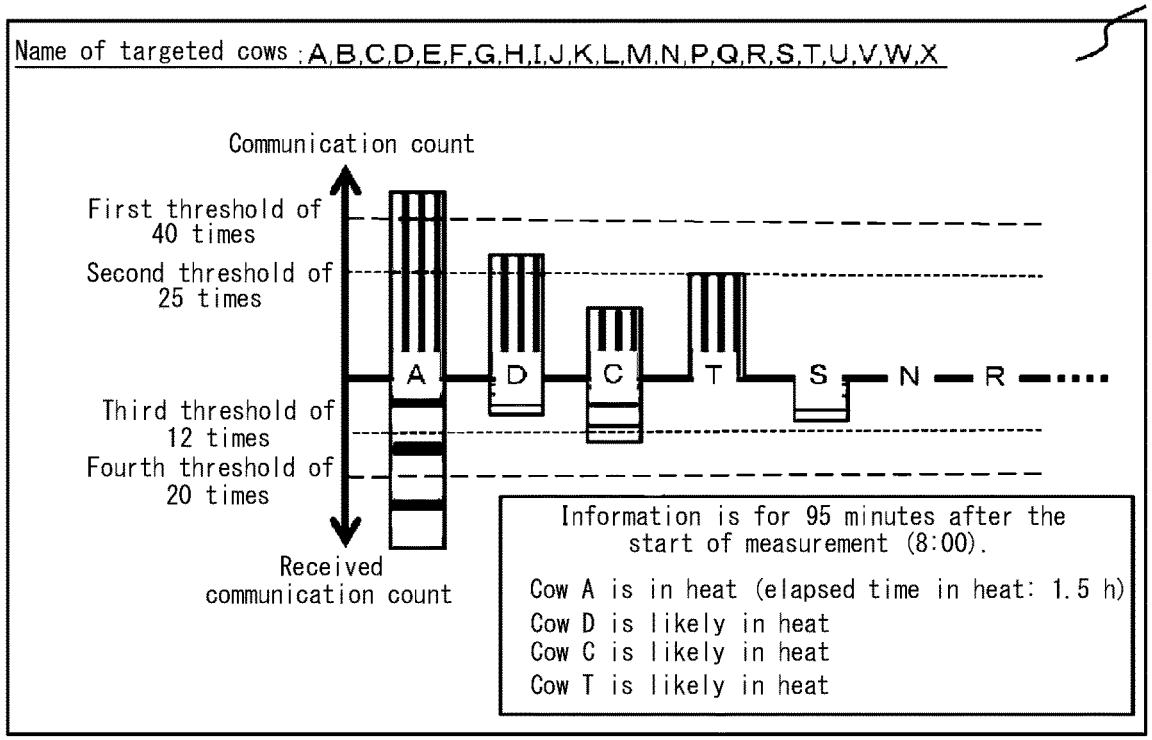
FIG. 7 illustrates an example of a screen on the user-side apparatus in the detection system.

The figures illustrate the results of collecting data from 8:00 in the morning (the start of grazing) until about 9:30 for a plurality of cows in the same pasture area. The leftmost bar for cow A in the graph in FIG. 7 is now described. FIG. 7 indicates the total of the number of times the mounting-side apparatus 10 of cow A communicated with the mounted-side apparatus 20 of another cow (mounting communication count) and the number of times the mounted-side apparatus 20 of cow A communicated with the mounting-side apparatus 10 of another cow upon cow A being mounted by the other cow (mounted communication count). Here, the mounting communication count of cow A exceeds a first threshold (40 times). The mounted communication count exceeds a fourth threshold of 20 times. The user-side terminal 30 may make the determination of the cow being in heat when the mounting communication count exceeds the first threshold, or when the mounting communication count exceeds the first threshold and the mounted communication count exceeds the fourth threshold.

Cow D is described next. The mounting communication count for cow D exceeds a second threshold of 25 times. In this case, the user-side terminal 30 determines that cow D is likely to be in heat. The mounted communication count for cow D does not exceed a third threshold, but a determination of the cow likely being in heat may be made when the mounting communication count exceeds the second threshold and the mounted communication count exceeds the third threshold.

As for cow C, the mounting communication count does not exceed either of the thresholds, but the mounted communication count exceeds the third threshold of 12 times. In this case, the user-side terminal 30 determines that cow C is likely to be in heat. Neither the mounting communication count nor the mounted communication count for cow T exceeds any of the thresholds, but since the mounting communication count matches the second threshold, the user-side terminal 30 determines that cow T may be in heat.

This bar graph is designed so that as the total communication count of a cow is higher, i.e. as the cow is more likely to be in heat, the bar is displayed further to the left of the screen. Comments regarding the probability of heat are also displayed within a box for cows that are in heat or may be in heat. Such comments are not essential, and while looking at the bar graph, the user may confirm whether cows are in heat on the basis of personal experience and the characteristics of each cow. For cows determined to be in heat, the elapsed time from the observation of the possibility of being in heat is displayed. The elapsed time is displayed because a good time to inseminate cows is between 0 hours and 24 hours, preferably between 5 hours and 16 hours, and more preferably between 8 hours and 13 hours, from the onset of heat. Furthermore, issues such as the thresholds and which of the mounting communication count and mounted communication count to give the most weight to are also affected by individual variation between cows. Hence, the conditions for identification may be settable for each user, and the user may be allowed to set the conditions for each cow.

Figure 8:
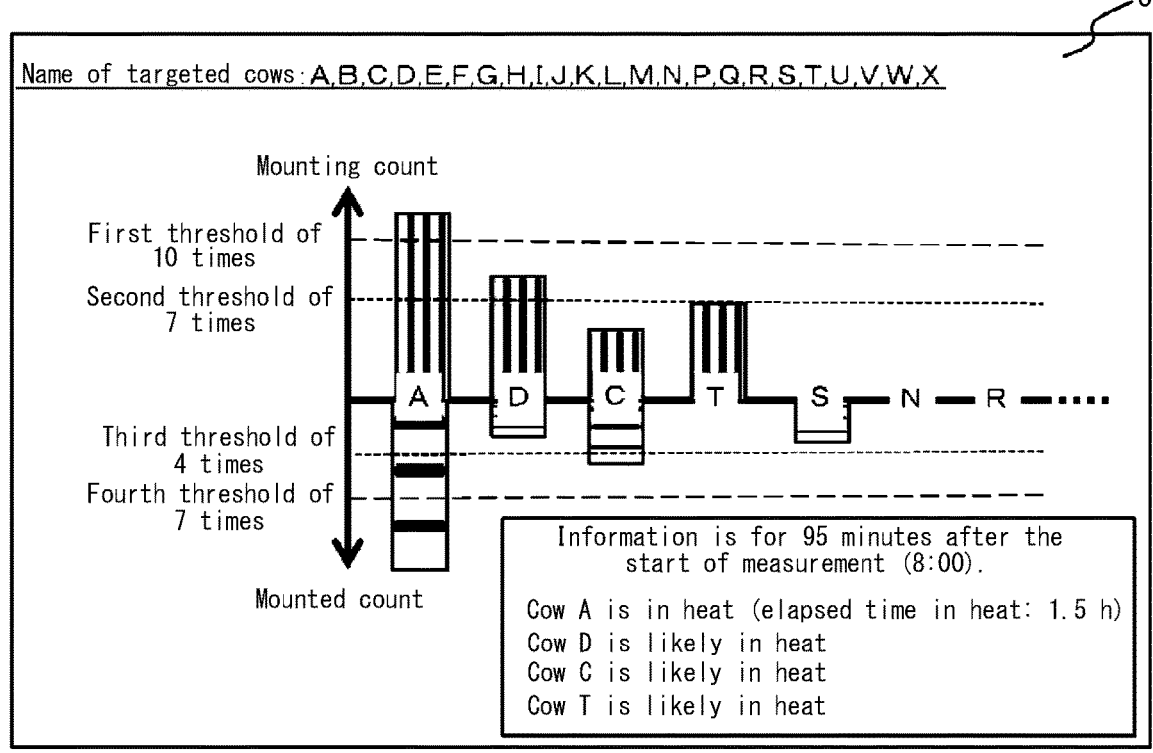
FIG. 8 illustrates an example of a screen on the user-side apparatus in the detection system.

The leftmost bar for cow A in the graph in FIG. 8 is now described. FIG. 8 indicates the total of the mounting count derived from the number of times the mounting-side apparatus 10 of cow A communicated with the mounted-side apparatus 20 of another cow and the mounted count derived from the number of times the mounted-side apparatus 20 of cow A communicated with the mounting-side apparatus 10 of another cow upon cow A being mounted by the other cow. Here, the mounting count of cow A exceeds a first threshold (10 times). The mounted communication count exceeds a fourth threshold of 7 times. The determination of the cow being in heat may be made when the mounting count exceeds the first threshold, or when the mounting count exceeds the first threshold and the mounted count exceeds the fourth threshold. In other words, the manufacturer or the user may be allowed to set a variety of determination conditions in accordance with factors such as the breeding environment, individual differences, and the type of domestic animal.

Cow D is described next. The mounting count for cow D exceeds a second threshold of seven times. In this case, the user-side terminal 30 determines that cow D is likely to be in heat. The mounted count for cow D does not exceed a third threshold of four times, but a determination of the cow likely being in heat may be made when the mounting count exceeds the second threshold and the mounted count exceeds the third threshold.

As for cow C, the mounting count does not exceed any of the thresholds, but the mounted count exceeds the third threshold of four times. In this case, the user-side terminal 30 determines that cow C is likely to be in heat. Neither the mounting count nor the mounted count for cow T exceeds any of the thresholds, but since the mounting count matches the second threshold, the user-side terminal 30 determines that cow T may be in heat.

Here, calculations may be made using a variety of algorithms to calculate the mounting (mounted) count from the mounting (mounted) communication count and to determine heat. Calculation examples using several algorithms are listed below.

During mounting behavior of a cow, the mounting cow continuously mounts the mounted cow for an average length of approximately two seconds to eight seconds. Consequently, the continuous mounting (mounted) time is two seconds to eight seconds on average during one episode of mounting behavior.

For example, the case of multiple instances of communication between the mounting-side apparatus 10 of cow A and the mounted-side apparatus 20 of cow B is considered. In this case, if the time from the first communication to the last communication (for example, six seconds) is within the aforementioned average continuous time of two seconds to eight seconds, the user-side terminal 30 may increment the mounting count of cow A and the mounted count of cow B each by one. In this case, one or more mounting-side apparatuses 10 may be arranged on cow A, and one or more mounted-side apparatuses 20 may be arranged on cow B. In other words, both the first communication and the last communication may be between any of the mounting-side apparatuses 10 on cow A and any of the mounted-side apparatuses 20 on cow B. In greater detail, when the first detected communication is with the mounted-side apparatus 20 disposed on the tail of the mounted cow B, communication occurs four seconds later with the mounted-side apparatus 20 on the back of the mounted cow B, and no subsequent communication occurs, then the continuous mounting time is taken to be four seconds, and the mounting (mounted) count is incremented by one.

Alternatively, as a simpler approach, when communication occurs between the mounting-side apparatus 10 of cow A and the mounted-side apparatus 20 of cow B a plurality of times, and the time from the first communication to the next communication (for example, three seconds) is within the aforementioned average continuous time of two seconds to eight seconds, the user-side terminal 30 may similarly increment the counts by one. As above, communication may be with any of the mounted-side apparatuses 20 of the same cow. Accordingly, whereas different IDs are assigned to the mounted-side apparatuses 20 of different cows, it poses no problem to assign the same ID to the mounted-side apparatuses 20 of the same cow. The memory (RFID chip) of the mounted-side apparatus 20 can thus be written to with a simple operation.

Conversely, for example when only an initial communication occurs, and the time until the next communication is outside of the aforementioned average continuous time of two seconds to eight seconds, or when only an initial communication occurs without any next communication, the user-side terminal 30 may count the mounting behavior as zero. In this case, however, the user-side terminal 30 may increment the chin resting by one. The reason is that communication detected by average chin resting is either one-time communication or has an extremely short time span. Since chin resting is also one index of heat, the determination of heat may include instances of chin resting.

As part of mounting behavior, a mounting cow exhibits behavior similar to chin resting by first resting its face by the mounted cow's buttocks or tail. At this time, when the mounted cow shows no signs whatsoever of heat, the mounted cow may refuse to be mounted and run away. In this case, communication is only detected once. Accordingly, chin resting (receipt of chin resting) may be counted once, without counting the mounting. A cow with a high chin resting count may be in heat, whereas it is often the case that a cow with a low mounted count but a high count of receipt of chin resting is refusing to be mounted. Hence, it may be determined that such a cow is likely not in heat.

On the other hand, when a mounted cow shows signs of being in heat, then upon chin resting or similar behavior, the mounted cow either remains relatively still and tolerates the subsequent mounting or exhibits gentle behavior such as escaping the subsequent mounting by walking a few steps forward during the mounting.

After chin resting or similar behavior, which is the initial step of mounting behavior, the mounting cow kicks the ground with its front legs and stands up. At the same time, the mounting cow's body shifts forward, from the tail towards the head of the mounted cow. Consequently, among a plurality of mounted-side apparatuses 20 attached to the same cow, communication with the mounted-side apparatus 20 attached by the buttocks or tail of the mounted cow is first detected. Communication with a mounted-side apparatus 20 further forward is detected next. Accordingly, the user-side terminal 30 may increment the mounting (mounted) count by one also when the position of the mounted-side apparatus 20, among the plurality of mounted-side apparatuses 20, that communicates moves forward from the back. When mounting is finished, the mounting cow's body shifts towards the back of the mounted cow. Detecting such a shift is also useful for mounting detection. In other words, the user-side terminal 30 may increment the mounting (mounted) count by one also when the mounted-side apparatus 20 that communicates first is disposed on the back, and subsequently communication is exchanged with a mounted-side apparatus 20 disposed on the tail. However, when communication is detected in the order of the tail, back, and tail during the aforementioned average mounting detection time, the mounting count is incremented by one so as not to be counted twice. During the aforementioned average mounting detection time, even if communication is exchanged with three or more mounted-side apparatuses 20, the count is increased by one, not by two or three. In other words, counting is not redundant. When following such an algorithm, the IDs allocated to the mounted-side apparatuses 20 need to differ between cows, and a different ID needs to be allocated at each position on the back, tail, or the like of the same cow. For example, the IDs as listed in the order of i) the left side, ii) atop the backbone, and iii) the right side on the back from the tail towards the head may be A-1L, A-2L, A-3L, . . . ; A-1M, A-2M, A-3M, . . . ; and A-1R, A-2R, A-3R, . . . for cow A; and B-1L, B-2L, B-3L, . . . ; B-1M, B-2M, B-3M, . . . ; and B-1R, B-2R, B-3R . . . for cow B.

Figure 9:
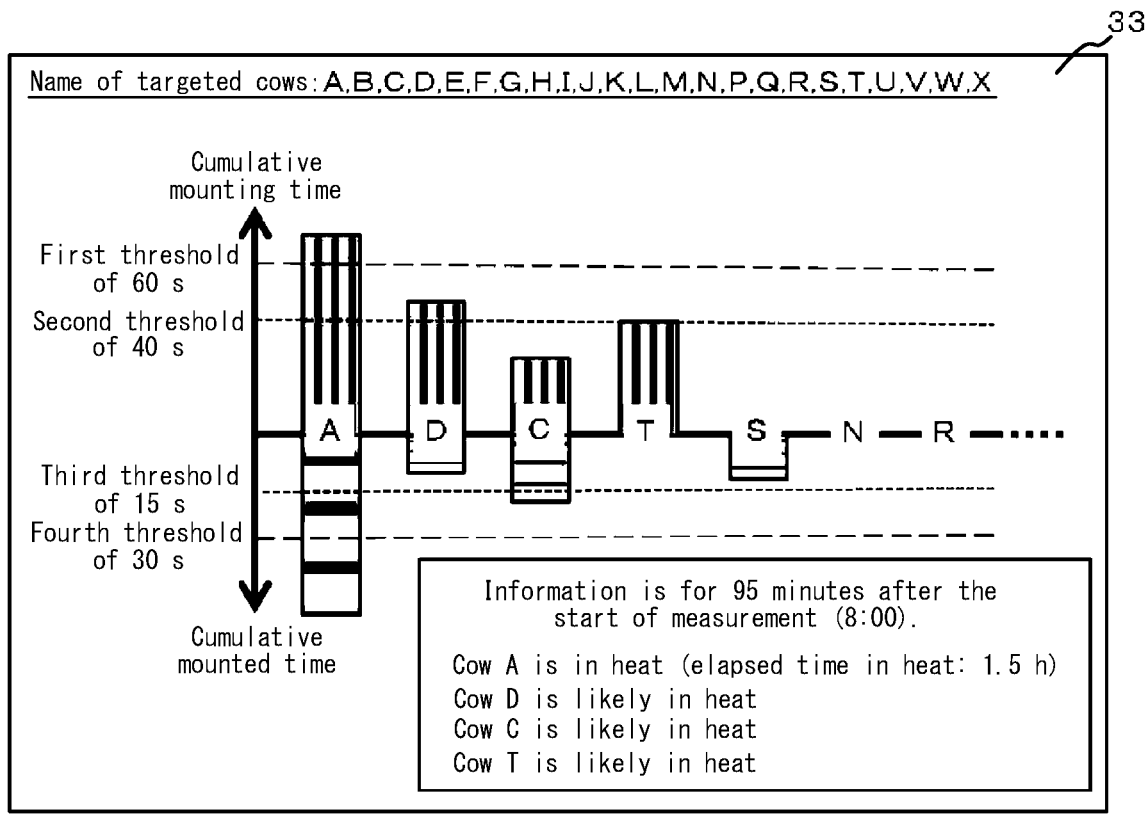
FIG. 9 illustrates an example of a screen on the user-side apparatus in the detection system.

The leftmost bar for cow A in the graph in FIG. 9 is now described. FIG. 9 indicates the cumulative mounting time derived from the length of time that the mounting-side apparatus 10 of cow A communicated with the mounted-side apparatus 20 of another cow and the cumulative mounted time derived from the length of time that the mounted-side apparatus 20 of cow A communicated with the mounting-side apparatus 10 of another cow upon cow A being mounted by the other cow. Here, the cumulative mounting time for cow A exceeds a first threshold of 60 seconds. The mounted communication count exceeds a fourth threshold of 30 seconds. The determination of the cow being in heat may be made when the mounting count exceeds the first threshold, or when the mounting count exceeds the first threshold and the mounted count exceeds the fourth threshold.

Cow D is described next. The cumulative mounting time for cow D exceeds a second threshold of 40 seconds. In this case, the user-side terminal 30 determines that cow D is likely to be in heat. The cumulative mounted time for cow D does not exceed a third threshold of 15 seconds, but a determination of the cow likely being in heat may be made when the cumulative mounting time exceeds the second threshold and the cumulative mounted time exceeds the third threshold.

As for cow C, the cumulative mounting time does not exceed either of the thresholds, but the cumulative mounted time exceeds the third threshold of 15 seconds. In this case, the user-side terminal 30 determines that cow C is likely to be in heat. Neither the cumulative mounting time nor the cumulative mounted time for cow T exceeds any of the thresholds, but since the cumulative mounting time matches the second threshold, it is determined that cow T may be in heat.

Here, calculations may be made using a variety of algorithms to calculate the continuous mounting (mounted) time and the cumulative mounting (mounted) time from the mounting (mounted) communication count and to determine heat. Calculation examples using several algorithms are listed below.

As described above, the continuous mounting (mounted) time is two seconds to eight seconds on average during one episode of mounting behavior. Accordingly, the simplest approach is for the user-side terminal 30 to increment the time by five seconds, which is the center value of the average mounting time, when communication occurs once or a plurality of times in an interval of two seconds to eight seconds.

Alternatively, during an interval of two to eight seconds, the user-side terminal 30 may record the elapsed time from the first communication to the last communication as the continuous mounting (mounted) time. Accumulating each continuous mounting (mounted) time for a plurality of mountings yields the cumulative mounting (mounted) time. In other words, the likelihood of heat is thought to be higher as the cumulative mounting time is longer, and the likelihood of heat is also thought to be higher as the cumulative mounted time is longer.

Conversely, for example when only an initial communication occurs, and the time until the next communication is outside of the aforementioned average continuous time of two seconds to eight seconds, or when only an initial communication occurs without any next communication, the user-side terminal 30 may count the continuous mounting time as zero.

As part of mounting behavior, a mounting cow exhibits behavior similar to chin resting by first resting its face by the mounted cow's buttocks or tail. At this time, when the mounted cow shows no signs whatsoever of heat, the mounted cow may refuse to be mounted and run away. On the other hand, when a mounted cow shows signs of being in heat, then upon chin resting or similar behavior, the mounted cow either remains relatively still and tolerates the subsequent mounting or exhibits gentle behavior such as escaping the subsequent mounting by walking a few steps forward during the mounting.

After chin resting or similar behavior, which is the initial step of mounting behavior, the mounting cow kicks the ground with its front legs and stands up. At the same time, the mounting cow's body shifts forward, from the tail towards the head of the mounted cow. Consequently, among a plurality of mounted-side apparatuses 20 attached to the same cow, communication with the mounted-side apparatus 20 attached by the buttocks or tail of the mounted cow is first detected. Communication with a mounted-side apparatus 20 further forward is detected next. Accordingly, the user-side terminal 30 may count the continuous mounting (mounted) time as follows when the position of the mounted-side apparatus 20 that communicates with a plurality of mounting-side apparatuses 10 moves forward from the back. Specifically, the user-side terminal 30 may count the difference in time between the communication time with the mounted-side apparatus 20 at the back (for example 8:25:00) and the communication time with the mounted-side apparatus 20 at the front (for example 8:25:03), i.e. a difference of three seconds, as the continuous mounting (mounted) time.

When mounting is finished, the mounting cow's body shifts towards the back of the mounted cow. Detecting such a shift is also useful for mounting detection. Specifically, the user-side terminal 30 may count the difference in time between the communication time with the initially communicating mounted-side apparatus 20 disposed on the back (for example 8:25:00) and the subsequent communication time with the mounted-side apparatus 20 disposed on the tail (for example 8:25:04), i.e. a difference of four seconds, as the continuous mounting (mounted) time. However, when communication is detected at the tail, back, and tail during the aforementioned average mounting detection time, the cumulative mounting time may be prevented from being counted twice by taking the difference between the initial and final communication times at the tail as the continuous mounting time.

When following such an algorithm, the IDs allocated to the mounted-side apparatuses 20 need to differ between cows, and a different ID needs to be allocated at each position on the back, tail, or the like of the same cow. For example, the IDs as listed in the order of i) the left side, ii) atop the backbone, and iii) the right side on the back from the tail towards the head may be A-1L, A-2L, A-3L, . . . ; A-1M, A-2M, A-3M, . . . ; and A-1R, A-2R, A-3R, . . . for cow A; and B-1L, B-2L, B-3L, . . . ; B-1M, B-2M, B-3M, . . . ; and B-1R, B-2R, B-3R . . . for cow B.

Figure 10:
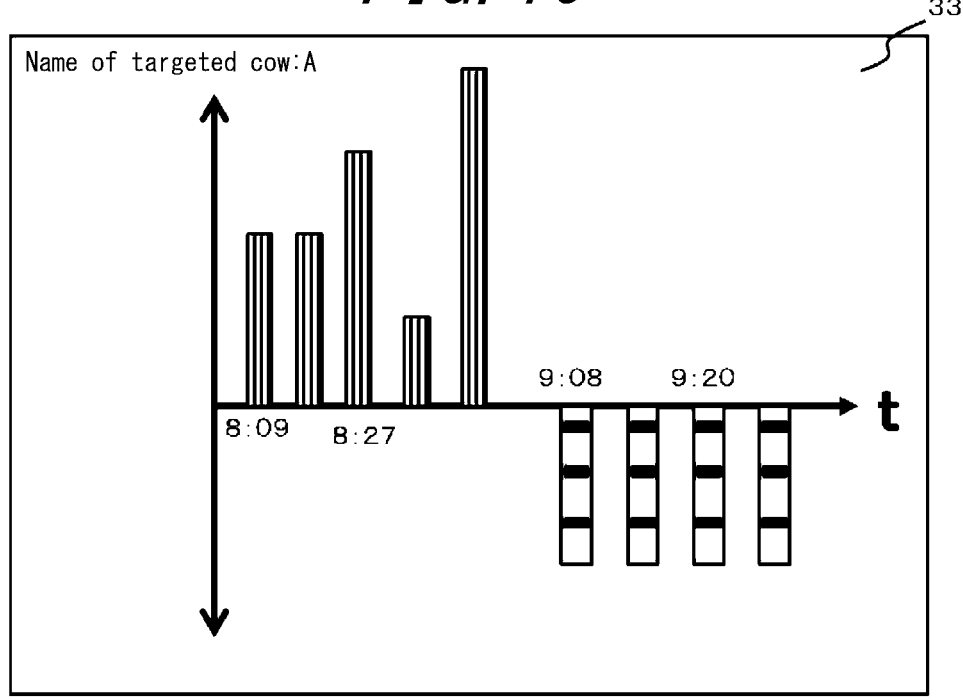
FIG. 10 illustrates an example of a screen on the user-side apparatus in the detection system.

Next, using FIG. 10, an example displaying a graph that illustrates the details of the heat behavior of cow A is described. Here, a configuration may be adopted to display the details of cow A illustrated in FIG. 10 upon touching the bar of cow A in FIGS. 7 through 9. In this case, the operation interface 36 may be a mouse of a PC or a touch panel.

The vertical axis represents the amount of activity for mounting behavior occurring between the start of measurement at 8:00 and the current time of 9:30, and the horizontal axis represents time. The amount of activity is, for example, the above-described mounting communication count in the positive direction and the above-described mounted communication count in the negative direction. Instead of the mounting communication count, the amount of activity may be the mounting (mounted) count, the cumulative mounting (mounted) time, the chin resting (receipt of chin resting) count, or the like. In the case of cow A, mounting behavior is detected between 8:00 and 9:00, and incidents of being mounted are observed from about 9:00. Cow A thus exhibits an acute state of heat. Since the elapsed time from the start of heat is approximately 1.5 hours, observation may be continued on the basis of a graph such as this one until reaching the suitable time slot for insemination (for example, 4 hours to 12 hours from the start of heat, more preferably 6 hours to 10 hours from the start of heat).

FIG. 11 illustrates details of the combination of communication logs, recorded in the memory of the mounting-side apparatus 10, for the mounting animal and the mounted animal. A configuration may also be adopted for these details to be displayed by operation of the operation interface 36 of the user-side terminal 30. The mounting communication records are accumulated in the mounting-side apparatus 10 with such logs. Each time a mounting communication log is recorded in this way, log information may be transmitted from the mounting-side apparatus 10 to the user-side terminal 30 through the communication interface of the second method. The log information may be transmitted to the user-side terminal 30 once approximately every 5 minutes or 10 minutes regardless of whether mounting behavior is detected (regardless of communication). Alternatively, one detection of mounting behavior or a certain number of detections of mounting behavior may serve as a trigger for the mounting-side apparatus 10 to transmit the log information. In this case, the mounting-side apparatus 10 may activate the communication interface 16 of the second method only when necessary without having to set the communication interface 16 continually on standby, as with a mobile phone or the like. This approach contributes to reduced power consumption.

Next, FIG. 12 illustrates an example of displaying a screen for selecting the subsequent action to take for target cow A. Here, four actions often taken after confirmation of heat are displayed as choices. The four choices are (1) whether to make an emergency call to a veterinarian, (2) whether to transmit mounting behavior information to a veterinarian, (3) whether to instruct a veterinarian to conduct artificial insemination, and (4) whether to continue observation. The contact information for the veterinarian or the like in (1) through (3) may be the telephone number or e-mail address of a pre-registered veterinarian, of an artificial inseminator, or of an employee on the pasture with authority over insemination. Configurations allowing selection of only one or of a plurality of these choices may be adopted.

The apparatuses in the disclosure and in the claims are referred to as a mounting-side apparatus and a mounted-side apparatus. The scope of the disclosure, however, is not limited to mounting of cows. The mounting-side apparatus includes any apparatus on an animal that mounts or exhibits chin resting, and the mounted-side apparatus includes any apparatus on an animal that is mounted or is the recipient of chin resting.

Accordingly, the aforementioned chin resting, detection of mounting behavior by horses or pigs, and detection of mating activity on the basis of mounting detection information are also included within the scope of protection of the disclosure. For example, the disclosure can also be applied to detection of copulatory behavior for natural breeding with a mounting-side apparatus 10 attached from the neck to in front of the chest of a male horse and a mounted-side apparatus 20 attached to the back of a female horse. The disclosure may also be similarly applied to pigs.

Figure 13:
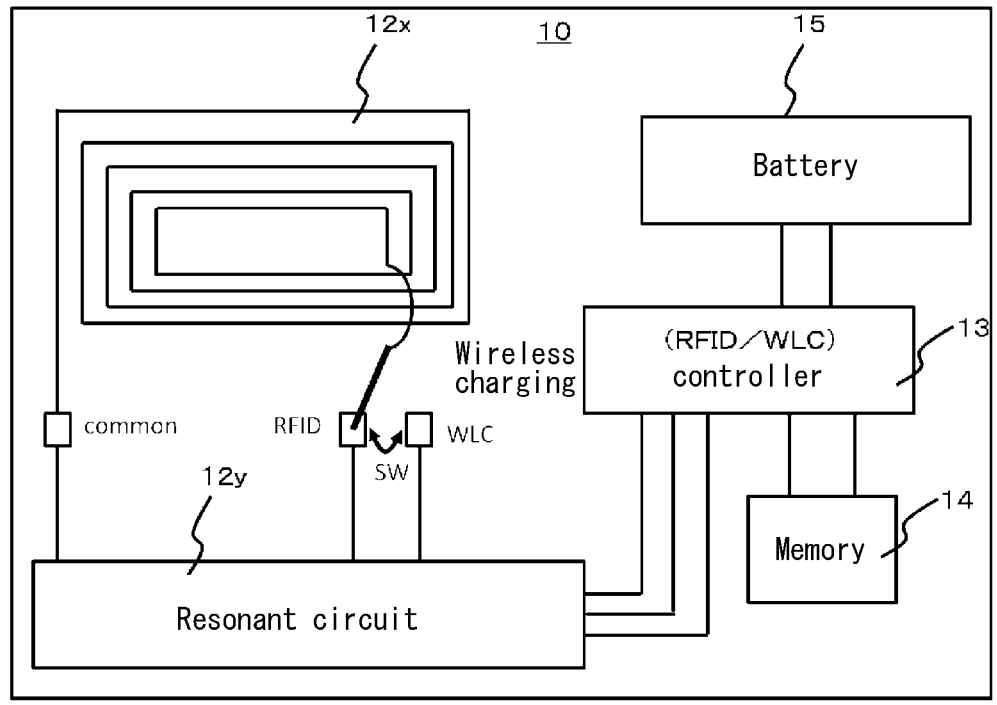
FIG. 13 illustrates an example of the circuit configuration of the mounting-side apparatus in the detection system.

The following configuration may also be adopted. For example, the mounting-side apparatus 10 may include a wireless charger for charging the power supply 15 without contact. As illustrated in FIG. 13, during wireless charging, an antenna (coil) 12x, a wireless charge (WLC) terminal, a resonant circuit 12y, the controller 13, and the power supply (battery) 15 are used. In other words, the constituent elements of the wireless charger include the antenna (coil) 12x, the wireless charge (WLC) terminal, the resonant circuit 12y, the controller 13, and the power supply (battery) 15.

By contrast, the communication interface 12 uses the antenna (coil) 12x, a radio frequency identifier (RFID) terminal, the resonant circuit 12y, and the controller 13 during RFID communication. The RFID terminal and the WLC terminal are switched between by a switching element SW. The controller 13 controls this switching.

Here, the antenna 12x and the resonant circuit are shared for use during both RFID communication (first method) and wireless charging (WLC). The (resonance) frequency band used for the wireless charging may, for example, be 13.56 MHz. In this case, the (resonance) frequency band used for the wireless charging may be the same as that of the RFID communication (first method). This case offers the advantage, for example, of being able to share the entire antenna coil 12x. It is also possible to share a portion of the antenna coil between different used frequency bands.

Figure 14:
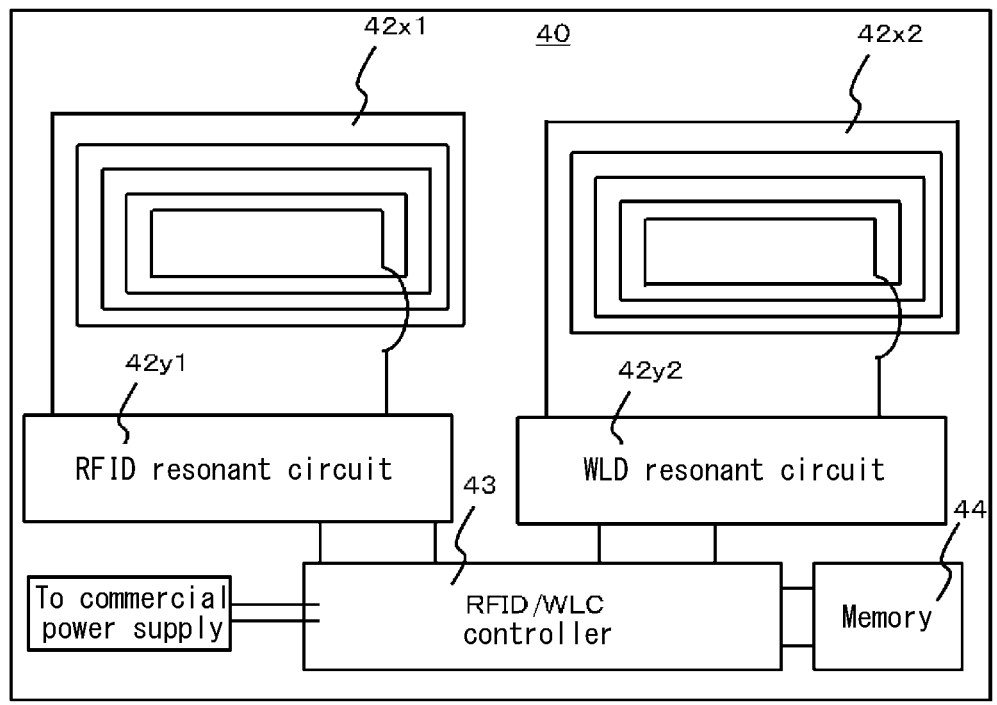
FIG. 14 illustrates an example of the circuit configuration of a charging apparatus in the detection system.

Next, the configuration of a charging apparatus 40 is illustrated in FIG. 14. The charging apparatus 40 includes a coil antenna 42x1 for WLC, a coil antenna 42x2 for RFID, respective resonant circuits 42y1, 42y2, a controller 43 for overall control of these components, and a memory 44.

Figure 15:
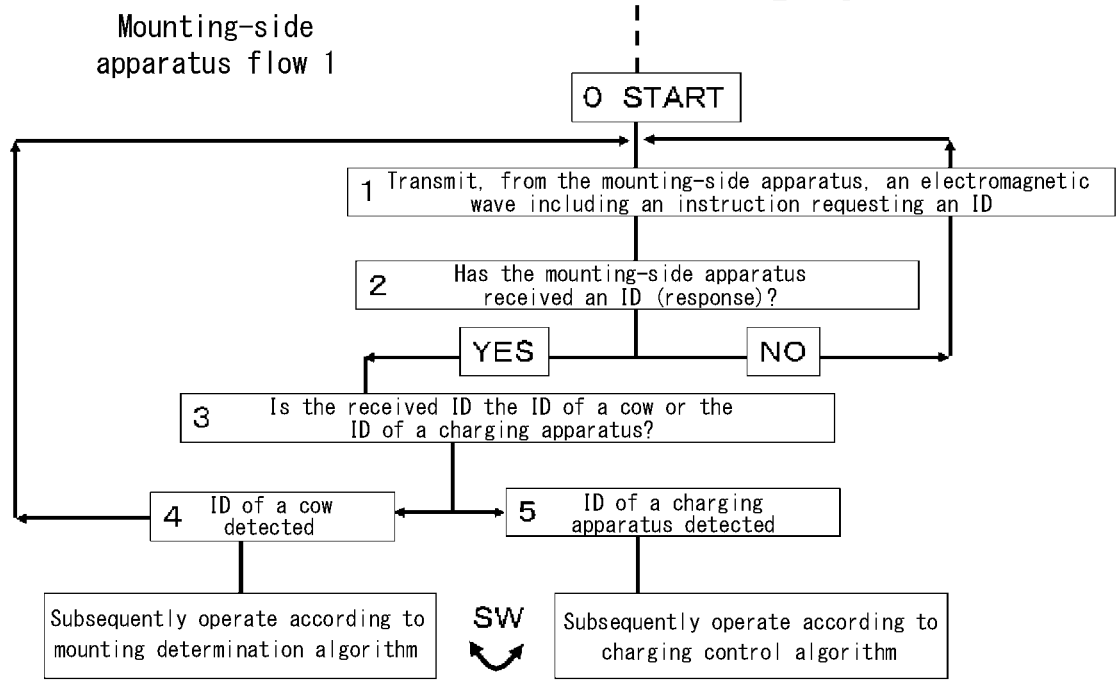
FIG. 15 illustrates an example of the control flow of the mounting-side apparatus in the detection system.

Next, the control steps of the mounting-side apparatus 10 and the charging apparatus 40 during charging are described. At a time such as when the cow or other domestic animal returns from the pasture area to the barn (though not limited to this time), the mounting-side apparatus 10 attached to the collar, the bridle, or the like is set on the charging apparatus 40 after being removed from the cow along with the collar or the like or being detached from the collar or the like. An example is described below with reference to FIG. 15 through FIG. 17. In FIG. 15, step 0 is indicated as the START, but this merely indicates the conceptual starting point for the sake of illustration, not an actual step. The mounting-side apparatus 10 may use the communication interface of the second method to communicate to the user-side terminal 30 that the remaining battery charge is low. The mounting-side apparatus 10 may be detached from the domestic animal in this case to start charging.

During RFID mode, the mounting-side apparatus 10 transmits an electromagnetic wave (transmission signal) at predetermined intervals (step 1 in FIG. 15). The transmission signal includes an instruction requesting that another apparatus transmit an ID. The charging apparatus 40 also receives the ID response request included in the transmission signal from the mounting-side apparatus 10 when the mounting-side apparatus 10 is placed on top of the charging apparatus 40 (step 13 in FIG. 17). Therefore, the charging apparatus 40 transmits the ID of the charging apparatus 40 to the mounting-side apparatus 10 (step 14 in FIG. 17). In the example in FIG. 14, the coil 42x1, the RFID resonant circuit 42y1, and the controller 43 are used at this time.

At this time, the mounting-side apparatus 10 that issued the ID response request included in the transmission signal is waiting for the response (ID information) from another apparatus (step 2 in FIG. 15). If the mounting-side apparatus 10 does not receive a response (ID information), the mounting-side apparatus 10 again transmits an electromagnetic wave, including an instruction requesting that another apparatus transmit an ID, at predetermined intervals (step 1 in FIG. 15). This is the case when no response is received at all, i.e. not only from the charging apparatus 40 but also from the mounted-side apparatus 20.

When a response is received, the mounting-side apparatus 10 uses the ID information included in the response to determine whether the received ID is the ID of a domestic animal, such as a cow, or the ID of the charging apparatus 40 (step 3 in FIG. 15).

The case of the ID included in the received response being the ID of a cow (a response from the mounted-side apparatus 20 of a cow) is described (step 4 in FIG. 15). In this case, the mounting-side apparatus 10 of the mounting behavior detection system performs the above-described operations on the basis of the received ID information, using an algorithm for determination of mounting. At the same time, the mounting-side apparatus 10 again transmits an electromagnetic wave including a transmission instruction requesting an ID from another apparatus (step 1 in FIG. 15). In other words, the process loops for a continuous state of monitoring mounting.

When the ID included in the received response is the ID of the charging apparatus, i.e. when the response is from the charging apparatus 40 (step 5 in FIG. 15), the mounting-side apparatus 10 subsequently operates in accordance with a charging control algorithm.

Details of a charging control algorithm according to an example are described with reference to FIG. 16 and FIG. 17. When the ID included in the received response is the ID of the charging apparatus (step 5 in FIG. 16), the mounting-side apparatus 10 checks on the voltage state of the battery. As the state of the battery, the mounting-side apparatus 10 determines, for example, whether the voltage exceeds 90% of the prescribed voltage level (step 6 in FIG. 16). In other words, when the voltage of the battery exceeds 90% of the prescribed voltage level, the mounting-side apparatus 10 determines that the battery is fully charged. If the battery is fully charged, the mounting-side apparatus 10 again transmits an electromagnetic wave, including a transmission instruction requesting an ID from another apparatus, at predetermined intervals without issuing any particular request to the charging apparatus 40 (step 1 in FIG. 15 or FIG. 16). In other words, the process loops for a continuous state of monitoring mounting.

Figure 16:
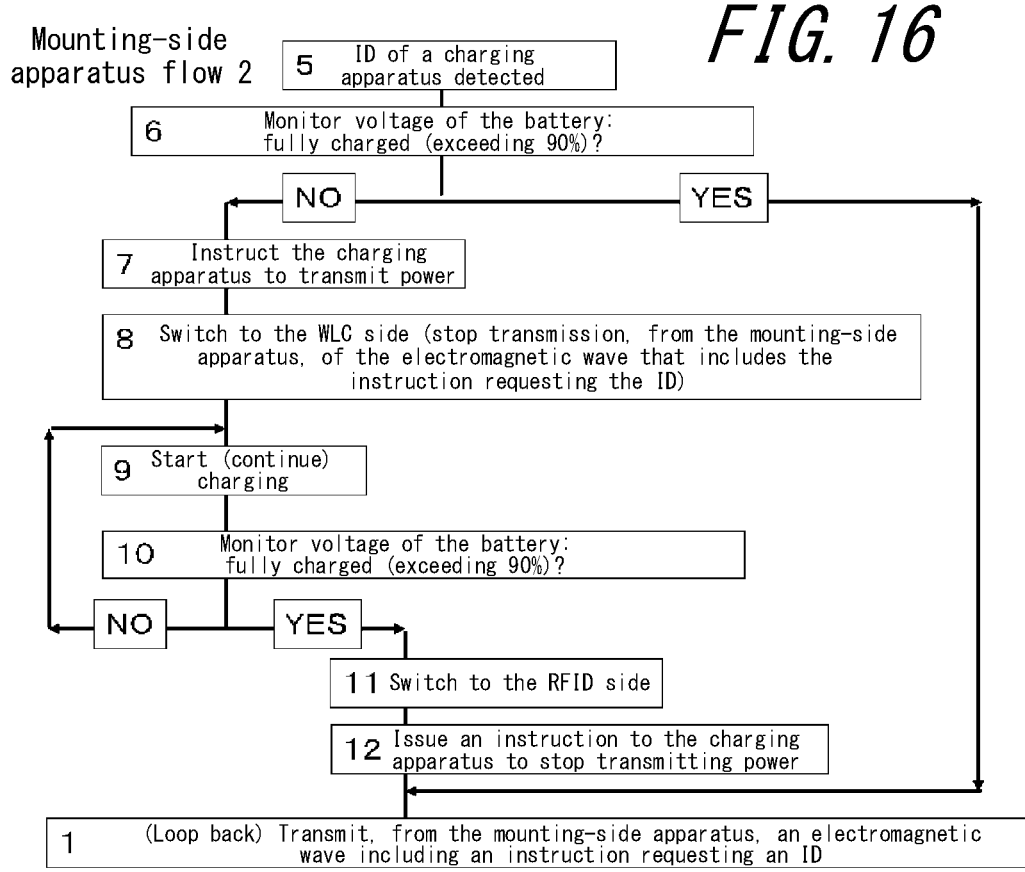
FIG. 16 illustrates an example of the control flow of the charging apparatus in the detection system.

If the battery is not fully charged (90% or less), the mounting-side apparatus 10 uses, for example, RFID transmission (first method) to instruct the charging apparatus 40 to transmit power (step 7 in FIG. 16). The instruction may be transmitted by the second method if a communication device of the second method is mounted in both the mounting-side apparatus 10 and the charging apparatus 40.

The mounting-side apparatus 10 then switches the connection from the RFID terminal to the WLC terminal with the switching element SW (step 8 in FIG. 16) so that the coil 12x that was being used in RFID communication is used for wireless charging (WLC).

Figure 17:
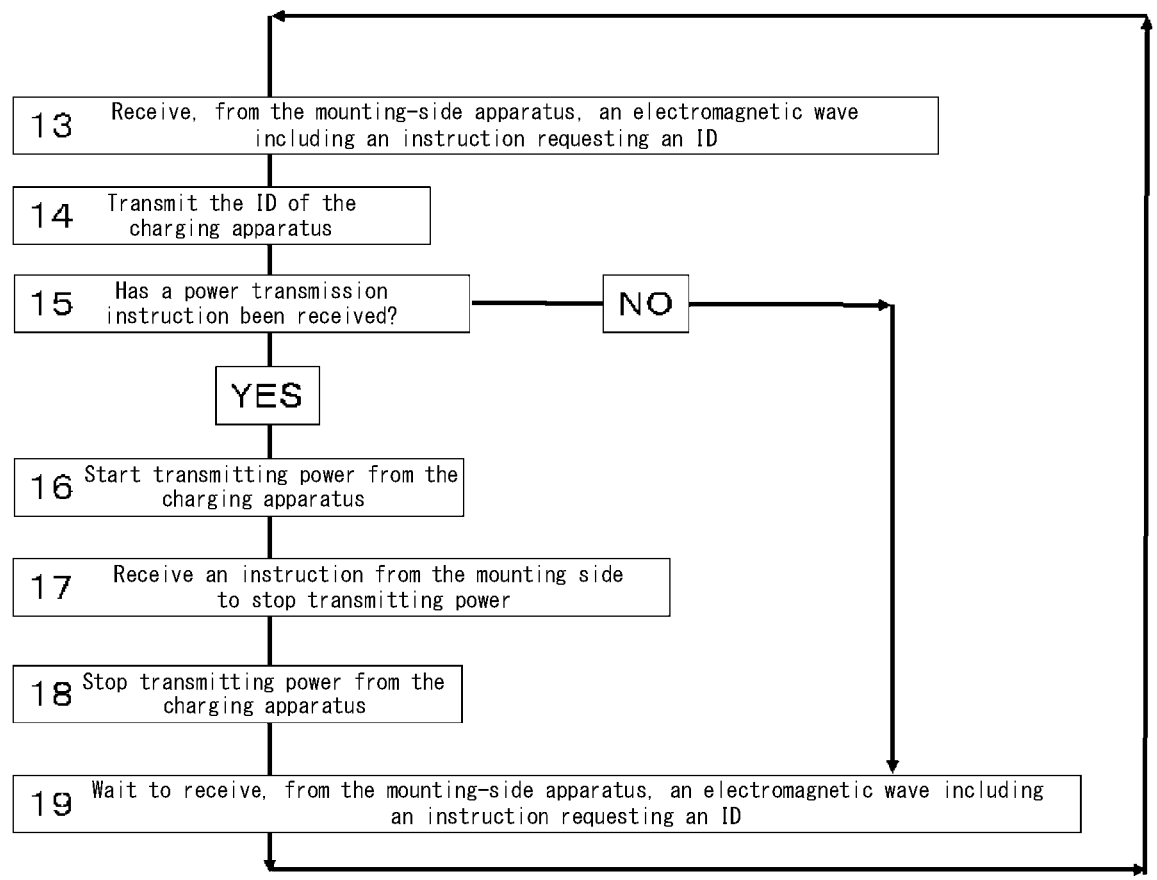
FIG. 17 illustrates an example of the control flow of the charging apparatus in the detection system.

When the charging apparatus 40 has not received a power transmission instruction from the mounting-side apparatus 10 (step 15 in FIG. 17: "NO"), the charging apparatus 40 returns to a state of waiting for reception of an electromagnetic wave, from the mounting-side apparatus 10, that includes an instruction requesting an ID (step 19 in FIG. 17).

Upon receiving a power transmission instruction from the mounting-side apparatus 10 (step 15 in FIG. 17: "YES"), the charging apparatus 40 starts to transmit power. In the example in FIG. 14, the coil 42x2, the WLC resonant circuit 42y2, and the controller 43 are used at this time. The charging apparatus 40 receives supply of power from a commercial power source.

Once power transmission from the charging apparatus 40 starts (step 16 in FIG. 17), the mounting-side apparatus 10 starts to charge the power supply (battery) using the received electromagnetic wave (step 9 in FIG. 16). The mounting-side apparatus 10 also monitors the voltage of the battery at this time to determine whether the battery is fully charged (step 10 in FIG. 16).

When the result of voltage monitoring indicates that the battery is not in a fully charged state (step 10 in FIG. 16: "NO"), the mounting-side apparatus 10 continues to charge (step 9 in FIG. 16). When the result of voltage monitoring indicates that the battery is in a fully charged state (step 10 in FIG. 16: "YES"), the mounting-side apparatus 10 switches the connection from the WLC terminal to the RFID terminal using the switching element SW (step 11 in FIG. 16). As a result, RFID communication becomes possible, and power reception (charging) automatically stops.

The mounting-side apparatus 10 then, for example, uses RFID communication to issue an instruction to the charging apparatus 40 to stop transmitting power (step 12 in FIG. 16). Subsequently, the mounting-side apparatus 10 again transmits an electromagnetic wave including a transmission instruction requesting an ID from another apparatus (step 1 in FIG. 15 and FIG. 16). In other words, the process loops for a continuous state of monitoring mounting.

Upon receiving an instruction from the mounting-side apparatus 10 to stop transmitting power, the charging apparatus 40 stops transmitting power (step 18 in FIG. 17). The charging apparatus 40 then returns to a state of waiting for reception of an electromagnetic wave, from the mounting-side apparatus 10, that includes an instruction requesting an ID (step 19 in FIG. 17).

An example of the mounting-side apparatus 10 sharing an antenna (coil) between an RFID mode and a WLC mode and an example of controlling the charging apparatus 40 with the first method that is RFID communication or the like have been described. The present disclosure is not, however, limited to these examples. As touched upon in the above-described example, when the mounting-side apparatus 10 and the charging apparatus 40 each include a communication interface of the second method, then the instruction from the mounting-side apparatus 10 to the charging apparatus 40 and the response to the instruction may be issued by the respective communication interfaces of the second method. In this case, the switching element SW for switching between the RFID terminal and the WLC terminal need not be provided. On the other hand, since the directivity is high in the case of control by the first method such as RFID communication, the risk of one mounting-side apparatus issuing a power transmission instruction or the like to many charging apparatuses (other charging apparatuses on which the mounting-side apparatus is not placed) is low, making it easy to manage a plurality of charging apparatuses.

Figure 18:
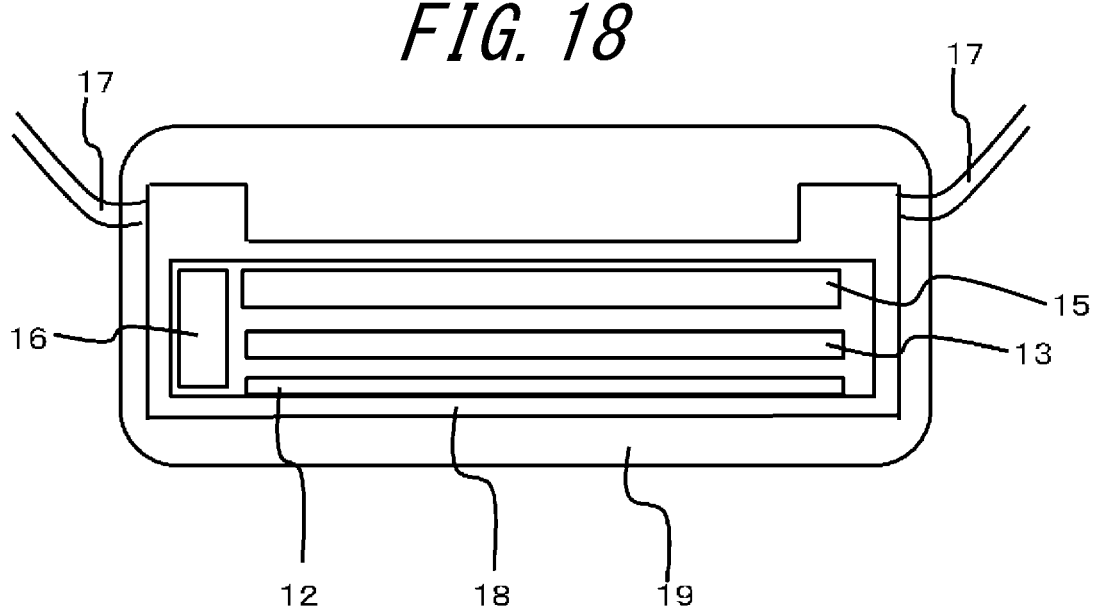
FIG. 18 illustrates an example of the structure of the mounting-side apparatus in the detection system.

Furthermore, by adopting a wireless charging method, the mounting-side apparatus 10 can be completely sealed by integrally molded resin. Specifically, all of the components of the mounting-side apparatus illustrated in FIG. 3 except for the holder 17 may be arranged within a mold and subsequently completely sealed by pouring the resin constituting the housing 18 into the mold. Alternatively, as illustrated in FIG. 18, the entire housing 18 may be placed inside a mold, and the resin that becomes the material of a sealing member 19 may be poured into the mold.

The mounting-side apparatus may be used only as long as recharging of the battery is possible and then discarded, or the mounting-side apparatus may be collected for recycling by the manufacturer, who may install a new battery and reseal with resin. This approach is easy to adopt when the first communication (RFID or IrDA), the second communication (for example, LTE, CDMA, BlueTooth®, WiFi), and the wireless charging (WLC) can all pass through resin. The various apparatuses are attached to the collar or bridle of an animal, easily become dirty, and are often exposed to rain or sand. The above-described complete sealing is a definite advantage for these apparatuses in terms of manufacturing, since it can be produced easily relative to the cost and is highly dustproof and waterproof.

A variety of plastics may be used as the resin. For example, an acrylic resin, a polyamide resin, a polycarbonate resin, an acrylonitrile/butadiene/styrene (ABS) copolymerized resin, and the like may be used as the resin. Alternatively, a silicone resin or a polyimide resin may also be used.

Furthermore, instead of molding, the method of manufacturing may be to form a sealing film on the entire exposed outer surface of the housing 18 and the like by dipping into a liquid precursor of the resin material. The aforementioned resins may be used as the resin in this case as well.

As described above, FIG. 3 is a schematic cross-sectional diagram of the mounting-side apparatus 10 and the mounted-side apparatus 20. In a portion of the description of FIG. 4 and the like, the mounted-side apparatus 20 is exemplified by an RFID tag configured by an IC chip. Neither the antenna (coil) $12x$ used in the communication interface 12 of the mounting-side apparatus 10 nor the antenna (coil) $21x$ used in the communication interface 21 of the mounted-side apparatus 20, however, is limited to the size of an IC chip used in a credit card or the like. A larger IC chip may be used. When installed in a smartphone or the like, IC chips include many other antennas, such as a 1 seg TV antenna or an antenna for CDMA, LTE, or the like. Considering the effect of noise on a display, such as an LCD, IC chips are often designed to be small. Products not for humans do not require a display or the like, however, and have few antennas, making it easy to reduce the IC chip in size.

Figure 19:
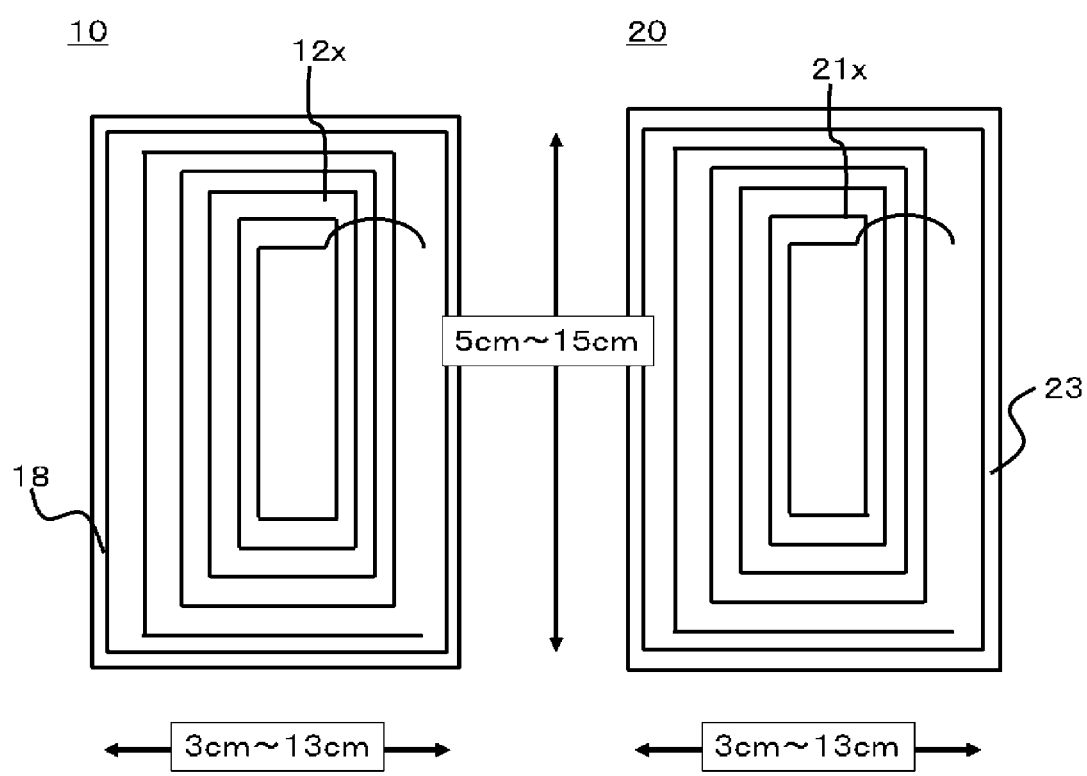
FIG. 19 illustrates an example of an antenna (coil) in the mounting-side apparatus and the mounted-side apparatus in the detection system.

For example, as illustrated in FIG. 19, the antenna (coil) $12x$ or the antenna (coil) $21x$ may be formed on nearly the entire principal surface of the housing 18 or the holding member 23. In this case, for example the coil can be produced to be from 5 cm to 15 cm high and from 3 cm to 13 cm wide. The coil can easily be formed by pattern design on a substrate, such as an FPC, using a conventional thin-film technique or a lamination technique. Also, the transmission-side coil and the reception-side coil may have approximately the same number of turns (one coil being within 80% to 120% of the other) and approximately the same vertical and horizontal diameter (one coil being within 80% to 120% of the other).

The invention claimed is:

1. A mounting behavior detection system comprising:
    a mounting-side apparatus attached to a neck or a chin of
        a first domestic animal, configured to emit a transmission signal, and including a battery;
    a mounted-side apparatus attached at any position from a
        back to a tail of a second domestic animal and configured to transmit a response signal in response to the transmission signal;
    a charging apparatus configured to transmit power wirelessly to the battery; and a wireless charger configured to receive power transmitted from the charging apparatus, wherein a communication interface is configured to transmit the transmission signal, and a coil or an antenna configuring the wireless charger also configures a coil or an antenna of the communication interface, and wherein a terminal at one end of the coil or the antenna is switched by a switch between connection with a radio-frequency identification terminal connected to the communication interface that emits the transmission signal and connection with a wireless charge terminal connected to the wireless charger.

2. The mounting behavior detection system of claim 1, wherein
the charging apparatus comprises a second communication interface configured to transmit a response signal in response to the transmission signal, and
upon the mounting-side apparatus transmitting the transmission signal and receiving a response signal in response to the transmission signal, the mounting-side apparatus determines whether the response signal is from the mounted-side apparatus or from the charging apparatus.

3. The mounting behavior detection system of claim 2, wherein the mounting-side apparatus maintains a mounting behavior detection mode when determining that the response signal is from the mounted-side apparatus.

4. The mounting behavior detection system of claim 2, wherein the mounting-side apparatus transitions to a charging mode when determining that the response signal is from the charging apparatus.

5. The mounting behavior detection system of claim 4, wherein upon the mounting-side apparatus transitioning to the charging mode, the mounting-side apparatus determines whether a voltage of the battery exceeds a predetermined voltage.

6. The mounting behavior detection system of claim 5, wherein the mounting behavior detection system returns to the mounting behavior detection mode when the voltage of the battery exceeds the predetermined voltage.

7. The mounting behavior detection system of claim 5, wherein when the voltage of the battery is equal to or less than the predetermined voltage, the mounting behavior detection system instructs the charging apparatus to transmit power using the coil or the antenna and stops transmission of the transmission signal.

8. A mounting behavior detection system comprising:
a mounting-side apparatus attached to a neck or a chin of a first domestic animal and configured to emit a transmission signal at a first cycle; and
a mounted-side apparatus attached at any position from a back to a tail of a second domestic animal and configured to transmit a response signal in response to the transmission signal; wherein
the mounting-side apparatus is sealed by a sealing member, and
upon receiving the response signal, the mounting-side apparatus is further configured to repeat transmission over a second cycle shorter than the first cycle.

9. The mounting behavior detection system of claim 8, wherein the sealing member comprises plastic including a resin selected from the group consisting of an acrylic resin, a polyamide resin, a polycarbonate resin, and an acrylonitrile/butadiene/styrene copolymerized resin.

10. The mounting behavior detection system of claim 8, wherein the mounting-side apparatus is sealed so that only the sealing member and a holder are exposed.

11. The mounting behavior detection system of claim 8, wherein the sealing member of the mounting-side apparatus and internal components to be sealed are fixed together by being molded integrally.

12. The mounting behavior detection system of claim 8, wherein the sealing member of the mounting-side apparatus is formed by immersing internal components to be sealed in a liquid precursor of the sealing member.

* * * * *